United States Patent [19]

Metz-Stavenhagen

[11] Patent Number: 5,330,472

[45] Date of Patent: Jul. 19, 1994

[54] DEVICE FOR APPLYING A TENSIONAL FORCE BETWEEN VERTEBRAE OF THE HUMAN VERTEBRAL COLUMN

[75] Inventor: Peter Metz-Stavenhagen, Bad Wildungen, Fed. Rep. of Germany

[73] Assignee: Howmedica GmbH, Schoenkirchen, Fed. Rep. of Germany

[21] Appl. No.: 714,473

[22] Filed: Jun. 13, 1991

[51] Int. Cl.$^5$ .............................................. A61B 17/56
[52] U.S. Cl. ....................................... 606/53; 606/60; 606/61
[58] Field of Search ........................... 606/61; 128/69; 623/17–23

[56] References Cited

U.S. PATENT DOCUMENTS

| 4,274,401 | 6/1981 | Miskew | 606/61 |
| 4,382,438 | 5/1983 | Jacobs | 606/61 |
| 4,409,968 | 10/1983 | Drummond | 128/69 |
| 4,422,451 | 12/1983 | Kalamchi | 606/61 |
| 4,611,582 | 9/1986 | Duff | 606/61 |
| 4,719,905 | 1/1988 | Steffe | 128/69 |
| 4,854,304 | 8/1989 | Zielke | 128/69 |
| 5,007,909 | 4/1991 | Rogozinski | 606/61 |
| 5,010,879 | 4/1991 | Moriya | 128/69 |
| 5,074,864 | 12/1991 | Cozad | 606/61 |

FOREIGN PATENT DOCUMENTS

| 0159007 | 10/1985 | European Pat. Off. . |
| 0328883 | 8/1989 | European Pat. Off. . |
| 3306657 | 9/1984 | Fed. Rep. of Germany . |
| 2289164 | 5/1976 | France . |
| 2131300 | 6/1984 | United Kingdom . |

Primary Examiner—Michael A. Brown
Attorney, Agent, or Firm—Peter C. Richardson; Lawrence C. Akers; Elizabeth O. Slade

[57] ABSTRACT

A device for applying a tensional force between two vertebrae of the human vertebral column, having at least two retaining members adapted to be brought into engagement with associated vertebrae, said members having a throughgoing opening for the accommodation of a threaded rod, and pairs of nuts adapted to be threaded onto said threaded rod in order to fix said retaining members in a desired position on said threaded rod, characterized in that said retaining members are configured as clamping members (10) having two legs (14, 16) which are bendable relative to each other in the plane extending through said threaded rod (26) to embrace a transverse process (22) of a vertebra.

7 Claims, 2 Drawing Sheets

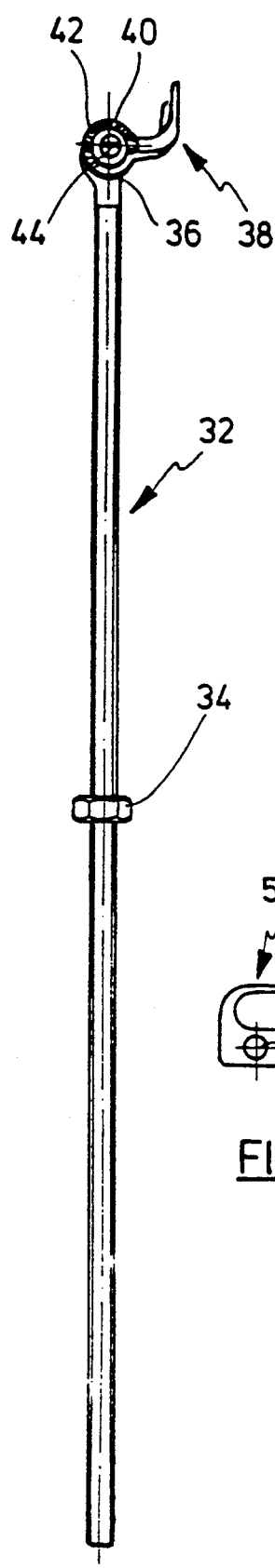
FIG.7
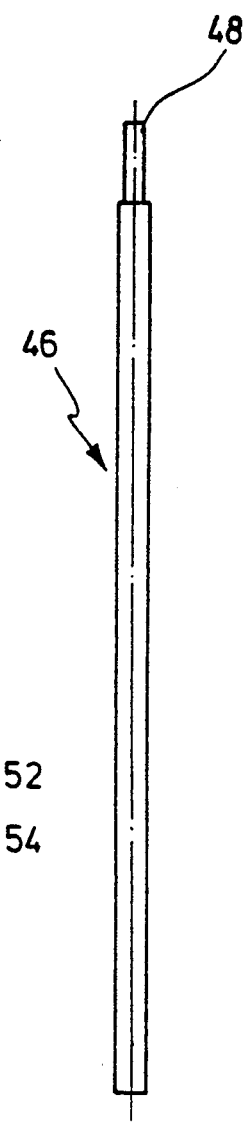
FIG.8
FIG.9
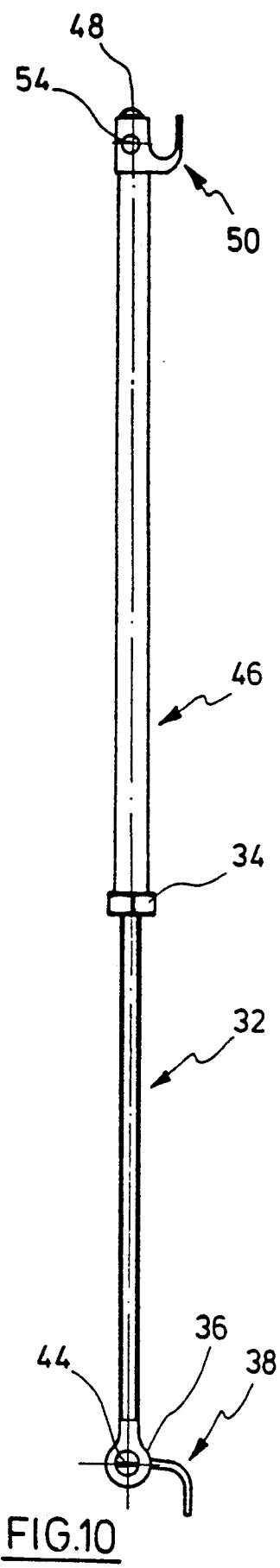
FIG.10

DEVICE FOR APPLYING A TENSIONAL FORCE BETWEEN VERTEBRAE OF THE HUMAN VERTEBRAL COLUMN

The invention refers to a device for applying a tensional force between vertebrae of the human vertebral column.

The German utility model 88 02 112 discloses a support device for the human vertebral column comprising so-called pedicle screws adapted to be threaded into the pedicles of the vertebrae. The pedicle screws have clamping surfaces co-operating with threaded bolts which for example may be adjusted by a threaded sleeve in order to change the attachment points where the pedicle screws are attached.

With the aid of the known support device, more than one vertebra can be overbridged, and a primary stabilization of the vertebra with respect to all degrees of freedom is achieved.

With the aid of the known support device, a compression and a distraction force as well can be exerted. It is also known to use other devices which exclusively distract or compress in addition to or instead of the known support device using pedicle screws. Normally, the other known devices use so-called lamina hooks which are mounted on a threaded rod. From the British patent specification 2 131 300, a device has become known which can be used for compression purposes and which uses lamina hooks. The U.S. Pat. No. 4,382,438 discloses a distraction device also using lamina hooks. A similar device of this kind is disclosed by the French patent specification 2 289 164.

In many cases, it is impossible to use pedicle screws, e.g. if the available bone substance does not allow a sufficiently secure seat of the pedicle screw in the vertebrae. If lamina hooks are used, it may occur that the hooks slide off and lose their support. In this case, an uncomfortable surgical re-operation is required. A surgical re-operation is also necessary if the lamina hooks are to be displaced relative to each other, i.e. if the patient is still growing.

The object of the invention is to provide a device for applying a tensional force between vertebrae of a human vertebral column which is simply structured and can be simply implanted.

With the device according to the invention, the transverse processes of the vertebrae define the engagement points for the compression or distraction device. The retaining members are configured as clamps having two legs which can be bent relative to each other in order to completely or partially embrace a transverse process. Such clamping members co-operate with a known threaded rod in that they are positioned on the threaded rod by nuts threaded onto the rod. The axis of the throughgoing openings of the clamps accommodating the threaded rod extends in or parallel to the plane defined by the legs of the retaining member.

In an embodiment of the invention, one leg of the retaining member is relatively rigid and arcuately curved while the other leg is relatively thin and bendable. The relatively rigid leg is to resist compression or distraction forces while the bendable leg serves for the attachment of the retaining member to the transverse process in order to fix the retaining member to the transverse process.

In order to facilitate the attachment of the retaining member to the transverse process, an embodiment of the invention provides that the portion of the thin leg adjacent to the opening is arcuately curved in its undeformed state while the other portion of the leg towards its free end is straight. The length of the thin leg is appropriately dimensioned such that the end of the rigid leg is overlapped if the thin leg is bent toward the rigid leg.

If the portion defining the opening of the retaining member is formed as a closed ring, the retaining member must be slided onto the threaded rod from one end thereof. Under certain circumstances, this is relatively difficult during a surgical operation. Therefore, an embodiment of the invention provides that the annular portion defining the opening includes a lateral slot having a width which corresponds approximately to the diameter of the threaded rod. Thus, the retaining member can be mounted on the threaded rod at an arbitrary axial position and fixed to the rod by opposite nuts on the threaded rod. In order to improve the access, the described slot is preferably arranged at an angle to the plane of the legs. This, however, means that different retaining members are required for the left and right side of the vertebral column.

As already mentioned above, the support devices using lamina hooks have to be adjusted to a predetermined distance therebetween which cannot be changed without a relatively heavy surgical operation. An improvement of the invention provides that the distance between the lamina hooks can be continuously changed. According to the invention, this device is characterized by a retaining member mounted on one end of an elongated tube which slidably accommodates a threaded rod, a further lamina hook may be mounted on the free end of the tube. A nut is threaded onto the threaded rod to engage the tube slided onto the threaded rod. With this structure, the lamina hooks are coupled through a telescopic connection which can be changed in its length by turning the nut on the threaded rod. If the growth of the patient requires to increase the distance between the lamina hooks, only a small incision has to be made in the area of the nut in order to displace the tube supporting the lamina hook relative to the threaded rod.

The mounting of the lamina hook on the described telescopic connection can be carried out by various kinds of constructions. According to an embodiment of the invention, the free end of the threaded rod includes an eyelet, one side thereof being roughened, particularly having a toothing while the associated lamina hook has an annular portion, one side thereof being also roughened, particularly provided with a toothing, with the eyelet and the annular portion being adapted to be clamped together by a threaded connection. The described attachment allows the change of the angular position of the lamina hook relative to the threaded rod.

The lamina hook associated with the tube is approximately mounted on a pin at the end of the tube and is fixed for example by means of a set screw. Such a lamina hook is generally known. In the device of the invention, the lamina hook, however, engages a shoulder of the tube so that an optional set screw merely secures the rotational position of the lamina hook. An additional axial fixation of the lamina hook is not necessary.

The invention will be explained in detail hereinafter with the aid of examples of the embodiments illustrated in the drawings.

FIG. 7 shows a threaded rod for a distraction device according to the invention.

FIG. 8 shows a lamina hook for the distraction device according to the invention.

FIG. 9 shows a tube for the distraction device according to the invention.

FIG. 10 shows the assembly of the parts shown in FIGS. 7 to 9.

Figure 1:
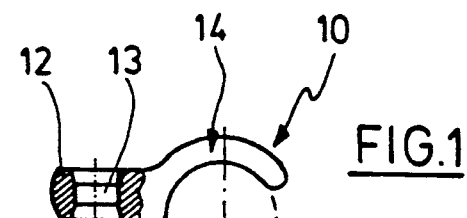
FIG. 1 is a side view partial in cross section of a retaining member according to the invention in its undeformed state.
Figure 2:
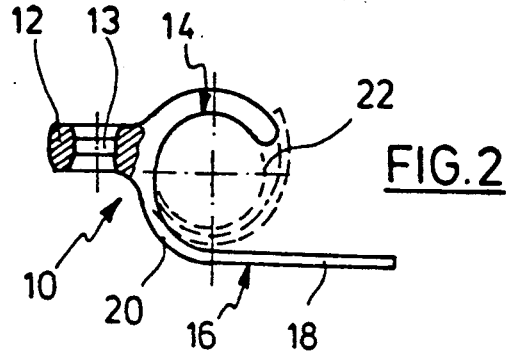
FIG. 2 is a similar illustration as FIG. 1 indicating the deformed state.

The retaining member 10 shown in FIG. 1 includes an annular portion 12 having a throughbore 13 which is conically enlarged toward its ends. Two legs 14, 16 are integrally formed with the annular portion, with the leg 14 being arcuate and made of relatively thick material. Leg 14 is relatively rigid. Leg 16 has a reduced thickness and has a portion 20 adjacent to the annular portion 12 which is arcuately curved, portion 20 merging into a straight portion 18. It can be seen in FIG. 2 that leg 16 can be bent as indicated by dashed lines. Leg 16 overlaps the rigid leg 14 and may embrace the transverse process of a vertebra of a human vertebral column, the transverse process being indicated by doted line 22. Thus, the retaining member 10 is fixedly secured to the transverse process.

Figure 3:
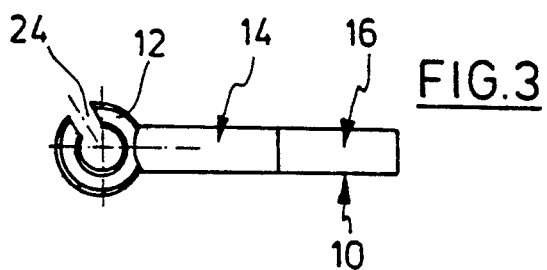
FIG. 3 is a side view of the retaining member of FIG. 1 for the left side of the vertebral column.
Figure 4:
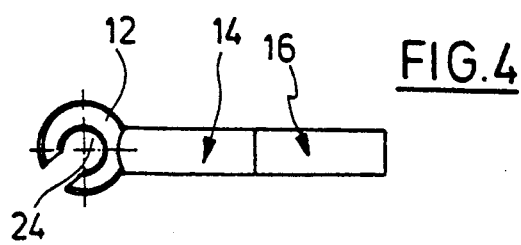
FIG. 4 is a similar illustration as FIG. 3 for the right side of the vertebral column.
Figure 5:
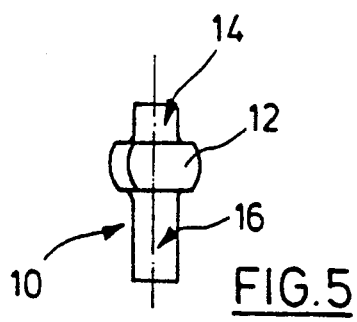
FIG. 5 is a rear view of the retaining member of FIG. 1.

As can be seen in FIGS. 3 and 4, annular portion 12 has a radial slot 24 extending at an angle to the plane defined by legs 14, 16. The orientation of the slots 24 depends upon which side of the vertebral column the retaining member 10 is to be placed. The retaining member of FIG. 3 is intended for the left side and the retaining member of FIG. 4 is intended for the right side of the vertebral column.

Figure 6:
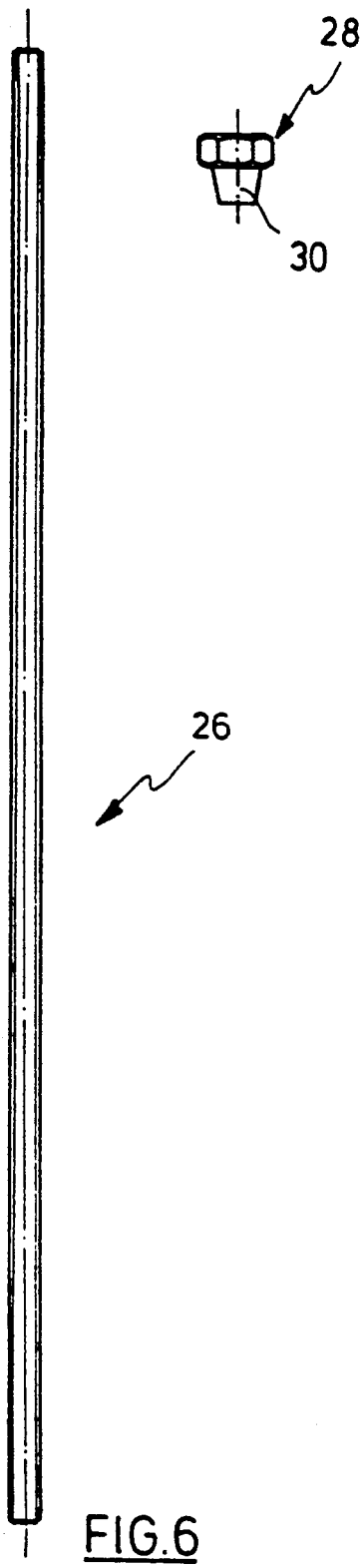
FIG. 6 shows a threaded rod for the retaining member illustrated in the FIGS. 1 to 5 and a nut for the fixation of the retaining member on the threaded rod.

A threaded rod 26 according to FIG. 6 is extended through the bore of the retaining members. Two nuts, one of which being shown at 28, can be threaded onto threaded rod 26 to attach retaining member 10. Nut 28 has a conical extension 30 which engages a corresponding conical portion of bore 13 in order to effectively fix the retaining member 10 to the threaded rod. In case two vertebrae are to be compressed, a retaining member of FIG. 1 is used for the upper vertebra and a retaining member which is turned about 180° is used for the lower vertebra so that for each retaining member, the rigid leg 14 is subject to the forces occuring.

In FIG. 7, a threaded rod 32 is illustrated onto which a conventional nut 34 is threaded. One end of the threaded rod 32 is provided with an eyelet 36 having a lateral surface provided with a toothing (not shown). A lamina hook 38 has an annular portion 40, one side or both sides thereof being also toothed as shown at 42. Eyelet 36 and annular portion 40 are clamped together by means of a threaded connection 44, with the toothing withstanding a relative rotation of hook 38 with respect to threaded rod 32.

A tube 46 is shown in FIG. 9 having an opened lower end and a closed upper end, with the closed end being provided with a cylindrical pin 48. Pin 48 serves to locate a lamina hook 50 shown in FIG. 8 and having a retaining portion 52 with a throughbore (not shown). With the aid of the throughbore, hook 50 can be placed on pin 48 as can be seen in FIG. 10. A transverse bore 54 may accommodate a set screw in order to fix the rotational position of hook 50 on tube 46.

It can be seen in FIG. 10 that tube 46 is slided onto threaded rod 32, with nut 34 limiting the relative movement of the parts. Thus, nut 34 defines the distance between the lamina hooks 38, 40. In case this distance is to be enlarged, e.g. by growth of the patient, only nut 34 is to be rotated in order to achieve an adjustment to the desired distance.

I claim:

1. A device for applying an adjustable tensional force between two vertebrae of the human vertebral column, said device comprising:
    (a) a first retaining member and a second retaining member to be brought into engagement with a first associated vertebra and a second associated vertebra and said first retaining member having a first throughbore and said second retaining member having a second throughbore;
    (b) a threaded rod which can be accommodated simultaneously within both said firth throughbore and said second throughbore;
    (c) an elongated tube having an unthreaded inner and outer surface which is dimensioned so that said threaded rod can e slid into said tube; and
    (d) a nut which threads onto said threaded rod and which contacts said tube so as to support said tube on said threaded rod and so as to adjust the position of said tube on said threaded rod, thereby adjusting the distance between said first retaining member and said second retaining member and thus adjusting the tensional force between said first associated vertebra and said second associated vertebra.

2. A device according to claim 1 and including also fastening means for fastening said first retaining member onto one end of said threaded rod and for fastening said second retaining member onto one end of said elongated tube.

3. A device according to claim 1, wherein said first retaining member is a first lamina hook.

4. A device according to claim 3, wherein said second retaining member is a second lamina hook.

5. A device according to claim 4, wherein said threaded rod has an eyelet at a first end thereof, wherein said eyelet has a side provided with a first toothing, and wherein said first lamina hook has an annular portion provided with a second toothing which meshes with said first toothing, and wherein said eyelet and said annular portion are clamped together by means of a threaded connection.

6. A device according to claim 4, wherein said first end of said rod includes a pin onto which a first lamina hook having a first throughbore can be placed.

7. A device according to claim 6, wherein said first lamina hook has a transverse bore for the accommodation of a set screw.

* * * * *